United States Patent
Su et al.

(10) Patent No.: US 11,744,524 B2
(45) Date of Patent: Sep. 5, 2023

(54) STATISTICAL DISPLAY METHOD FOR PHYSIOLOGICAL PARAMETER OF MONITORING APPARATUS, AND MONITORING APPARATUS

(71) Applicants: SHENZHEN MINDRAY BIO-MEDICAL ELECTRONICS CO., LTD., Shenzhen (CN); SHENZHEN MINDRAY SCIENTIFIC CO., LTD., Shenzhen (CN)

(72) Inventors: Jianwei Su, Shenzhen (CN); Zehui Sun, Shenzhen (CN); Zehong Guan, Shenzhen (CN); Xianliang He, Shenzhen (CN); Wenyu Ye, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 582 days.

(21) Appl. No.: 16/894,985

(22) Filed: Jun. 8, 2020

(65) Prior Publication Data
US 2020/0297283 A1  Sep. 24, 2020

Related U.S. Application Data

(63) Continuation of application No. PCT/CN2017/115288, filed on Dec. 8, 2017.

(51) Int. Cl.
*A61B 5/00* (2006.01)
*A61B 5/024* (2006.01)
(Continued)

(52) U.S. Cl.
CPC ........ *A61B 5/7264* (2013.01); *A61B 5/02405* (2013.01); *A61B 5/02455* (2013.01);
(Continued)

(58) Field of Classification Search
CPC .............. A61B 5/7264; A61B 5/02405; A61B 5/02455; A61B 5/316; A61B 5/363; A61B 5/364; A61B 5/366; A61B 5/743
See application file for complete search history.

(56) References Cited

U.S. PATENT DOCUMENTS 6,117,074 A    9/2000  Schuermann et al.
6,993,377 B2   1/2006  Flick et al.
(Continued)

FOREIGN PATENT DOCUMENTS

CN    102138789 A    8/2011
CN    103876718 A    6/2014
(Continued)

OTHER PUBLICATIONS

International Search Report issued in corresponding International Application No. PCT/CN2017/115288, dated Sep. 5, 2018, 4 pages.
First Office Action issued in related Chinese Application No. 201780098075.X, dated Mar. 29, 2023, 7 pages.

*Primary Examiner* — Scott M. Getzow
(74) *Attorney, Agent, or Firm* — BAYES PLLC

(57) ABSTRACT

This disclosure provides a monitoring apparatus and a statistical display method for physiological parameter(s) thereof. The method may include receiving statistical setting information including a time range, a time interval, a classification rule, and a target parameter, and the classification rule may define one or more types of the target parameter; obtaining N group of target parameter result corresponding to N time interval from a result of historical physiological parameter, where the N time interval is included in the time range, and the N group of target parameter result may be a
(Continued)

physiological parameter result corresponding to the target parameter in the result of historical physiological parameter; counting the number of each type of the target parameter in the N group of target parameter result according to the classification rule, and obtaining N group of statistical result corresponding to the N time interval for each target parameter.

20 Claims, 6 Drawing Sheets

(51) Int. Cl.
    *A61B 5/0245*     (2006.01)
    *A61B 5/316*     (2021.01)
    *A61B 5/363*     (2021.01)
    *A61B 5/364*     (2021.01)
    *A61B 5/366*     (2021.01)

(52) U.S. Cl.
    CPC .............. *A61B 5/316* (2021.01); *A61B 5/363* (2021.01); *A61B 5/364* (2021.01); *A61B 5/366* (2021.01); *A61B 5/743* (2013.01)

(56) References Cited

U.S. PATENT DOCUMENTS

| | | | |
|---|---|---|---|
| 2015/0005656 A1* | 1/2015 | Lee | G16H 40/67 600/523 |
| 2015/0051462 A1* | 2/2015 | Olsen | A61B 5/743 600/323 |
| 2017/0128735 A1* | 5/2017 | Gustavson | A61B 5/7445 |

FOREIGN PATENT DOCUMENTS

| | | |
|---|---|---|
| CN | 104095621 A | 10/2014 |
| CN | 106709256 A | 5/2017 |

* cited by examiner

STATISTICAL DISPLAY METHOD FOR PHYSIOLOGICAL PARAMETER OF MONITORING APPARATUS, AND MONITORING APPARATUS

CROSS-REFERENCE TO RELATED APPLICATIONS

This disclosure is a bypass continuation of Patent Cooperation Treaty Application No. PCT/CN2017/115288, filed on Dec. 8, 2017. This application is hereby incorporated by reference.

TECHNICAL FIELD

This disclosure relates to the technical field of medical equipment, and particularly to a statistical display method for physiological parameter of a monitoring apparatus, a monitoring apparatus and computer readable medium.

BACKGROUND

With the development of the times and the advancement of technology, the medical level has also been greatly improved. Since a monitoring apparatus can provide important patient information for medical clinical diagnosis, it has been widely used. The monitoring apparatus is a practical precision medical equipment in the hospital, which can monitor the physiological parameter(s) of a patient in real time and provide a basis for emergency response and treatment to the doctor. The physiological parameters measured and monitored by the monitoring apparatus may include ECG (Electrocardiograph) signal, EMG (Electromyography) signal, blood oxygen signal, EEG (ElectroEncephalo Graph) signals, etc. The monitoring apparatus can receive the patient's ECG signals, perform QRS wave detection and classification on the ECG signals, distinguish normal heartbeat and ventricular premature beat, and calculate and display in an interface of the monitoring apparatus physiological parameters such as heart rate, the number of ventricular premature beat per minute, arrhythmia alarm, etc. Also, the monitoring apparatus can record the historical waveform of the ECG signal, the trend chart of the heart rate and the number of ventricular premature beat per minute, and the event list of the arrhythmia alarm.

Ventricular premature beat is common in those patients with heart disease. It can be secondary to any type of heart disease, and its influences on the human body are also very different in different situations. The ventricular premature beat which is mild can have no influence, while which is severe can cause fatal arrhythmias such as ventricular tachycardia and ventricular fibrillation. The severity of the ventricular premature beat can be classified by the frequency and morphological changes of the ventricular premature beat. If medical staff want to know the recent ventricular premature beat information of the patient, they can do this by: viewing the patient's ECG historical waveform and distinguishing the frequency or the morphology of the ventricular premature beat, which costs a lot of precious time of the medical staff; viewing the trend chart of the number of ventricular premature beat per minute, which trend chart can only reflect the corresponding number of ventricular premature beat per minute at each time; viewing the event list of the arrhythmia alarm related to the ventricular premature beat, in which case the event of the ventricular premature beat may not be recorded when the switch of the corresponding alarm type is turned off. In addition, if the medical staff wants to know the patient's other physiological information in the recent period, they also need to do so through such similar approach.

The disadvantage of the above technical solution is that the operation is complicated and it takes a lot of time for the medical staff.

SUMMARY

In a first aspect, an embodiment of this disclosure can provide a statistical display method for physiological parameter(s) of a monitoring apparatus. The method may include: receiving and/or extracting statistical setting information, where the statistical setting information may include a time range, a time interval, a classification rule, and a target parameter, and the classification rule may define one or more types of the target parameter; obtaining N group of target parameter result corresponding to N time interval from a result of historical physiological parameter, where the N time interval is included in the time range, and the N group of target parameter result may be physiological parameter result corresponding to the target parameter in the result of historical physiological parameter; counting the number of each type of the target parameter in the N group of target parameter result according to the classification rule, and obtaining N group of statistical result corresponding to the N time interval for each type of the target parameter; and displaying the N group of statistical result.

In a second aspect, an embodiment of this disclosure may provide a monitoring apparatus. The monitoring apparatus may include a unit, such as a processor, for performing the method of the first aspect.

In a third aspect, an embodiment of this disclosure may provide another monitoring apparatus, including a processor, an input device, an output device, and a memory, where the processor, the input device, the output device and the memory can be connected with each other. The memory may be used for storing a computer program for supporting a terminal to execute the above-described method. The computer program may include program instructions, and the processor can be configured to invoke the program instructions to perform the method of the first aspect.

According to a fourth aspect, an embodiment of this disclosure may provide a computer readable storage medium that stores a computer program, where the computer program may include program instructions, which when executed by a processor can cause the processor to implement the method of the first aspect described above.

In the embodiment of this disclosure, the monitoring apparatus can receive the statistical setting information, calculate the target parameter according to the statistical setting information, and display the statistical result. Also, it can intuitively display the statistical result of the target parameter according to the user's setting information, thus achieving simple operation.

BRIEF DESCRIPTION OF THE DRAWINGS

In order to more clearly explain the technical solutions in the embodiments or the background of this disclosure, the drawings required in the embodiments or the background of this disclosure will be described below.

DETAILED DESCRIPTION OF EMBODIMENTS

Figure 1:
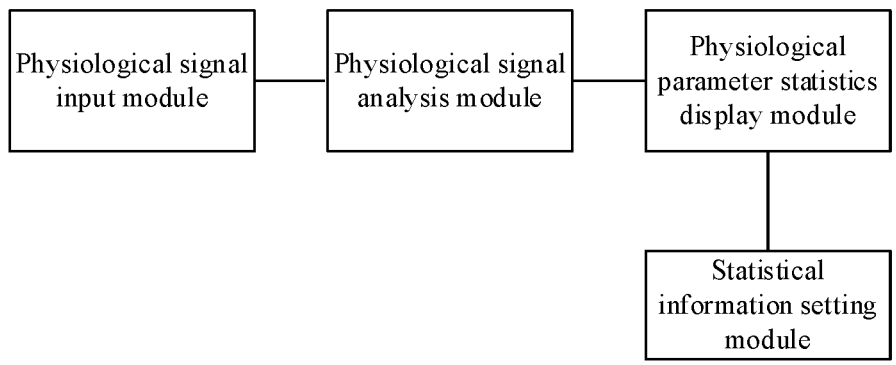
FIG. 1 is a schematic structural diagram for a monitoring apparatus provided by an embodiment of this disclosure.

In order to make the objectives, technical solutions and advantages of this disclosure clear, this disclosure will further be described in detail below with reference to the accompanying drawings.

It should be noted that the detailed descriptions set forth in connection with the accompanying drawings are intended as descriptions of various configurations, and are not intended to represent as the only configuration for implementing the concepts described herein. The device embodiments and the method embodiments described herein will be described in the following detailed descriptions, and will be shown in the accompanying drawings through various blocks, modules, units, components, circuits, steps, processes, algorithms, etc. (collectively referred to as "Element"). These elements can be implemented using electronic hardware, computer software, or any combination thereof. Whether these elements are implemented as hardware or software depends on the specific application and design constraints imposed on the overall system. If those terms such as "first" and "second" are used in the specification and claims of this disclosure and the accompanying drawings in the specification, this description is used to distinguish different objects, rather than describing a specific order.

It should be understood that the terms such as "including" and "comprising", when used in this specification and the appended claims, indicate the presence of the described features, wholes, steps, operations, elements, and/or components, but do not exclude the presence or addition of one or more other features, wholes, steps, operations, elements, components, and/or combinations thereof. It should also be understood that the terms used in the description of this disclosure herein is only for the purpose of describing particular embodiments and is not intended to limit this disclosure. As used in the specification and the appended claims of this disclosure, unless otherwise indicated herein, the singular forms of "a", "an", and "the" are intended to include the plural forms. It should also be further understood that the term "and/or" used in the specification and the appended claims of this disclosure refers to any and all possible combinations of one or more associated and listed items.

It should be noted that the respective technical features in the embodiments of this disclosure can be considered to be capable of being combined with each other without clear specific instructions, as long as the combination is not practical due to technical reasons. In order to fully illustrate this disclosure, some exemplary, optional, or preferred features are described in conjunction with other technical features in the embodiments of this disclosure. Such conjunction is not necessary, and it should be understood that those exemplary, optional, or preferred features are all separable or independent of the other technical features, as long as such separability or independence is not impossible for technical reasons. Some functional descriptions of the technical features in the method embodiments can be understood as performing the function, the method or the step, and some functional descriptions of the technical features in the device embodiments can be understood as using the device to perform the function, the method or the step.

An embodiment of this disclosure may provide a statistical display method for physiological parameter(s) of a monitoring apparatus. The method may include steps of physiological signal acquisition, physiological signal analysis, statistical information setting and statistical display of physiological parameter.

The monitoring apparatus may use a physiological signal input module or a physiological signal acquisition device to acquire the physiological signal of a patient. The physiological signal input module may acquire the physiological signal or obtain the physiological signal from other devices. The physiological signal may include electrocardiographic signal (ECG signal), myoelectric signal (EMG signal), blood oxygen signal, and so on. For example, the monitoring apparatus may use its equipped physiological signal input module or a matched physiological signal acquisition device to collect the physiological signals of the patient. For another example, the monitoring apparatus may obtain the physiological signals from other physiological signal acquisition devices. As shown in FIG. 1, the monitoring apparatus may include the physiological signal input module, a physiological signal analysis module, a statistical information setting module, and a physiological parameter statistics display module. Here, the physiological signal input module can obtain the physiological signal of the patient; the physiological signal analysis module can analyze the input physiological signal to obtain a physiological parameter result; the statistical information setting module can set by a user a time range, a time interval, a classification rules and physiological parameter type information for statistical analysis; and the physiological parameter statistics display module can use the physiological parameter result and the set statistical information to perform statistical analysis and display the graphical statistical result.

Figure 2:
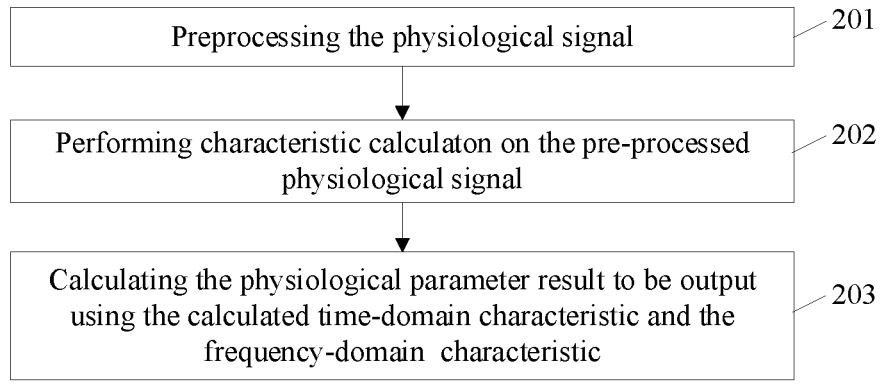
FIG. 2 is a processing flowchart of a physiological signal analysis module of a monitoring apparatus provided by an embodiment of this disclosure.

The physiological signal analysis module in the above-described monitoring apparatus can analyze the acquired physiological signal to obtain a result of historical physiological parameter. The processing flow of the physiological signal analysis module is shown in FIG. 2. In step 201, the physiological signal is pre-processed. For example, high-pass and low-pass filter processing is performed to filter out high-frequency noise and remove baseline drift. In step 202, characteristic calculation can be performed on the pre-processed physiological signal to calculate a time-domain characteristic (such as QRS wave position, QRS wave interval, QRS wave width, pulse wave position, etc.) and a frequency-domain characteristic (such as spectral power distribution, effective signal frequency peak position, etc.). In step 203, the physiological parameter result can be calculated using the calculated time-domain characteristic and the frequency-domain characteristic, and output to be the input of the physiological parameter statistics display module.

Figure 3:
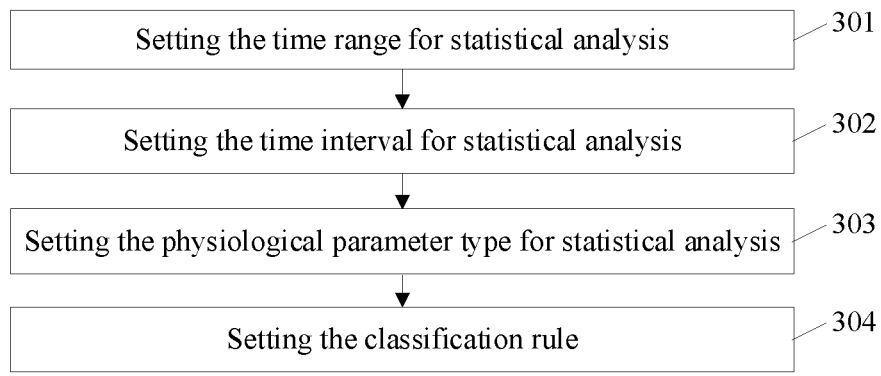
FIG. 3 is a processing flowchart of a statistical information setting module of a monitoring apparatus provided by an embodiment of this disclosure.

The statistical information setting module in the above-described monitoring apparatus can receive statistical setting information input by the user and perform the corresponding setting operations. The processing flow of the statistical information setting module is shown in FIG. 3. In step 301, the time range for statistical analysis can be set, that is, a start time and an end time of a statistical time period can be set. For example, the start time may be 6 hours ago and the end time is the current time. In step 302, the time interval for statistical analysis, that is, a time length of each statistical period can be set, such as 1 hour. In step 303, the physiological parameter type for statistical analysis can be set, that is, the physiological parameter that needs to be displayed statistically can be selected. For example, the selected physiological parameter can be ventricular premature beat, blood oxygen saturation and so on. In step 304, the classification rules, i.e., the classification rule of the physiological parameter type, can be set up. For example, the classification rule can be based on the number of consecutive ventricular premature beat, and the physiological parameter type can be divided into four types: a singular ventricular premature beat (1 V), two consecutive ventricular premature beats (2 V), short consecutive ventricular premature beats (3 to 5 V), long consecutive ventricular premature beats (more than 5 V), where V means a ventricular premature beat.

Figure 4:
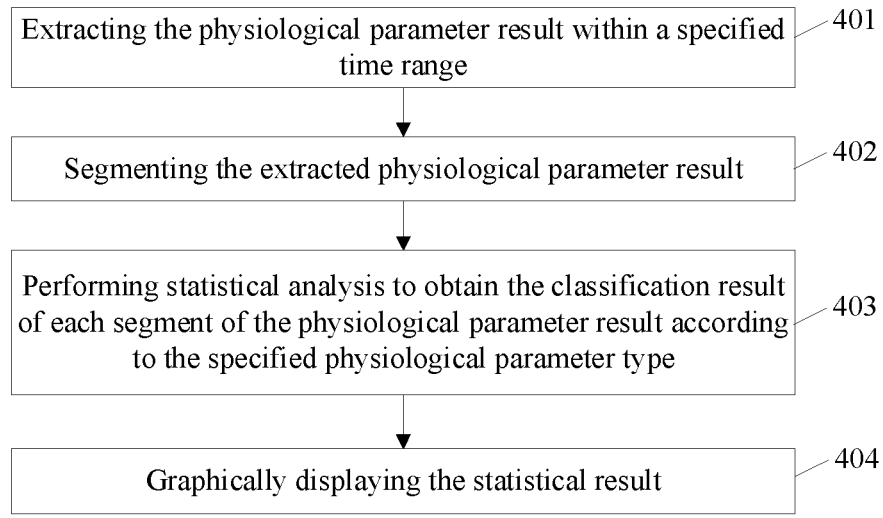
FIG. 4 is a processing flowchart of a physiological parameter statistics display module of a monitoring apparatus provided by an embodiment of this disclosure.

The physiological parameter statistics display module in the above-described monitoring apparatus may perform the statistical analysis on the physiological parameter result according to the statistical setting information, and can display the statistical analysis result. The processing flow of the physiological parameter statistics display module is shown in FIG. 4. In step 401, the physiological parameter result within a specified time range can be extracted from the result of historical physiological parameter. In step 402, the extracted physiological parameter result may be segmented according to a specified time interval. In step 403, the statistical analysis may be performed according to a specified physiological parameter type to obtain a classification result of each segment of the physiological parameter result, that is, the number of occurrence of the corresponding physiological parameter type may be counted according to the physiological parameter type specified by the user. In step 404, the statistical result may be displayed in a graphical way. That is, the statistical result of each segment of the physiological parameter result can be displayed graphically according to the time range and the time interval set by the user as well as according to the classification result of the specified physiological parameter type.

In the embodiment of this disclosure, the monitoring apparatus can perform the statistical analysis to obtain and further display the statistical result required by the user according to the statistical setting information input by the user, which is simple in the operation and time-saving.

Figure 5:
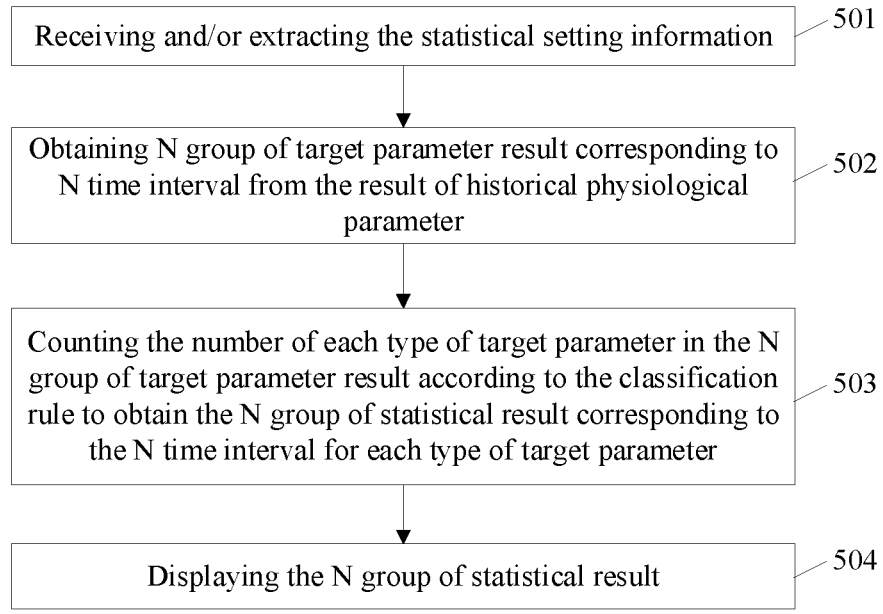
FIG. 5 is a statistical display method of physiological parameter(s) in a monitoring apparatus provided by an embodiment of this disclosure.

Please referring to FIG. 5, FIG. 5 is another statistical display method for physiological parameter of a monitoring apparatus according to an embodiment of this disclosure. The method may include the following steps 501 to 504.

In step 501, statistical setting information can be received and/or extracted. The statistical setting information can include a time range, a time interval, a classification rule, and a target parameter. The classification rule may define various types of the above-mentioned target parameter.

The receiving and/or extracting the statistical setting information may refer to receiving the statistical setting information input by a user, and correspondingly the statistical setting information is all input by the user. Or, the receiving and/or extracting the statistical setting information may refer to extracting the statistical setting information preset by the monitoring apparatus, and correspondingly the statistical setting information is all preset within the monitoring apparatus. Or, the receiving and/or extracting the statistical setting information may refer to both receiving a part of the statistical setting information input by the user and extracting another part of the statistical setting information from the monitoring apparatus to obtain the above-described statistical setting information. For example, the user may set the time range, the time interval, the classification rules and the target parameters. For another example, the monitoring apparatus may extract a preset time range, a preset time interval, a preset classification rule and a preset target parameter without the need of user setting. For another example, the user may set the time range and the target parameters, and the monitoring apparatus may extract the preset time interval and the preset classification rule. It can be understood that the above-described statistical setting information may all be set by the user; all may be extracted from the monitoring apparatus; or a part thereof may be set by the user, and another part thereof may be extracted from the monitoring apparatus. The above-described statistical setting information may also include other information, which is not limited in this embodiment of this disclosure.

The statistical setting information preset in the monitoring apparatus can be changed or set by the user. For example, the preset time interval of the monitoring apparatus can be 1 hour, and the user can set the time interval to be 30 minutes. For another example, the preset target parameter of the monitoring apparatus can be heart rate or pulse rate, the classification rule can be based on the range of the heart rate or the pulse rate, and the user can set the preset target parameter to be QRS wave interval, and adjust the classification rule to be based on the range of the heart rate corresponding to the QRS wave interval; where the target parameter according to the adjusted classification rule can be divided into five types: extreme bradycardia (HR<35 bpm), bradycardia (35 bpm<=HR<50 bpm), normal (50 bpm<=HR<=120 bpm), tachycardia (120 bpm<HR<=160 bpm), and extreme tachycardia (HR>160 bpm). It can be understood that the user can set the preset statistical setting information of the monitoring setting by himself. In some situations, the user can first set a part of the preset statistical setting information, and enter another part of the statistical setting information when it is needed to obtain and display the statistical result of the target parameter. In some situations, the user can first set all the preset statistical setting information, and the user does not need to do further setting when it is needed to obtain and display the statistical result of the target parameter.

The monitoring apparatus can receive the above-described statistical setting information through an input device; or the monitoring apparatus can also receive the statistical setting information sent by other devices through a receiver. For example, the user may input the statistical setting information through the input device of the monitoring apparatus, such as a keyboard, a setting button and a touch screen. For another example, the user may send the statistical setting information to the monitoring apparatus through a terminal such as a mobile phone. The above-described target parameter may be ventricular premature beat, QRS wave interval, heart rate, arrhythmia alarm event, etc., which is not limited in the embodiments of this disclosure. The above-described classification rule may define the classification method of the above target parameter. For example, when the target parameter is the heart rate or the pulse rate, the classification rule can be based on the range of the heart rate or the pulse rate, where target parameter can be divided into five types: extreme bradycardia (HR<35 bpm), bradycardia (35 bpm<=HR<50 bpm), normal (50 bpm<=HR<=120 bpm), tachycardia (120 bpm<HR<=160 bpm), and extreme tachycardia (HR>160 bpm), a total of five types. For another example, when the target parameter is the arrhythmia alarm event, the classification rule can be based on the alarm level, and thus the target parameter can be divided into four types: high-level alarm (cardiac arrest, ventricular fibrillation, ventricular tachycardia, ventricular bradycardia, extreme tachycardia, extreme bradycardia), medium-level alarm (R on T, polymorphic ventricular premature beat, ventricular premature beat bigeminy, ventricular premature beat trigeminy, bradycardia, tachycardia, unsustainable ventricular tachycardia, ventricular rhythm), low-level alarm (consecutive ventricular premature beat, heartbeat pause) and prompting alarm (two consecutive ventricular premature beat, singular ventricular premature beat, pacemaker not captured, pacemaker not paced, dropped beat, irregular rhythm, atrial fibrillation).

In step 502, N group of target parameter result corresponding to N time interval can be obtained from the result of historical physiological parameter. The N time interval can be included in the time range, and the N group of target parameter result may be the physiological parameter result corresponding to the target parameter in the result of historical physiological parameter.

The above-described monitoring equipment can acquire the physiological signal, perform corresponding analysis and processing, and obtain the physiological parameter result. For example, the monitoring apparatus can receive the patient's ECG signal, perform QRS wave detection and classification on the ECG signal, distinguish between normal heartbeat and ventricular premature beat, and calculate the physiological parameter result such as the heart rate and the arrhythmia alarm. The above-described result of historical physiological parameter may refer to the physiological parameter result before the current time instant. The above-described result of historical physiological parameter may include the results of multiple physiological parameters, or may only include the results of the target physiological parameter. For example, the result of historical physiological parameter may include the results of multiple physiological parameters (such as heart rate, QRS wave interval, and arrhythmia alarm) within a period of time before the current time instant; or the result of historical physiological parameter may only include the results of the target parameter within a period of time before the current time instant.

The N group of target parameter result corresponding to the N time interval obtained from the result of historical physiological parameter may refer to the target parameter result during N time period corresponding to the N time interval from the result of historical physiological parameter. For example, the time range is 6 hours, and the time interval is 1 hour. The entire time range includes 6 time intervals, and these 6 time intervals correspond to 6 time periods. The monitoring apparatus can thus obtain the target parameter result within these 6 time periods. The above-described result of historical physiological parameter may include the results of various physiological parameters such as the heart rate, the arrhythmia alarm event, the QRS wave interval, and the blood oxygen saturation. The N group of target parameter result is the physiological parameter result corresponding to the target parameter in the result of historical physiological parameter, for example, the physiological parameter result corresponding to the QRS wave interval.

In step 503, the number of each type of the target parameter in the N group of target parameter result may be counted according to the classification rule, and accordingly N group of statistical results corresponding to the N time interval can be obtained for each type of the target parameter.

The above-described monitoring apparatus may be preset with the classification rules of the target parameter; or the user may set the classification rule of the target parameter. For example, when the target parameter is ventricular premature beat, the classification rule can be based on the number of consecutive ventricular premature beat, which can be divided into four types: singular ventricular premature beat, two consecutive ventricular premature beat, short consecutive ventricular premature beat, and long consecutive ventricular premature beat. The monitoring apparatus can count the number of these four types of ventricular premature beats.

In step 504, the above N group of statistical result can be displayed.

Figure 6:
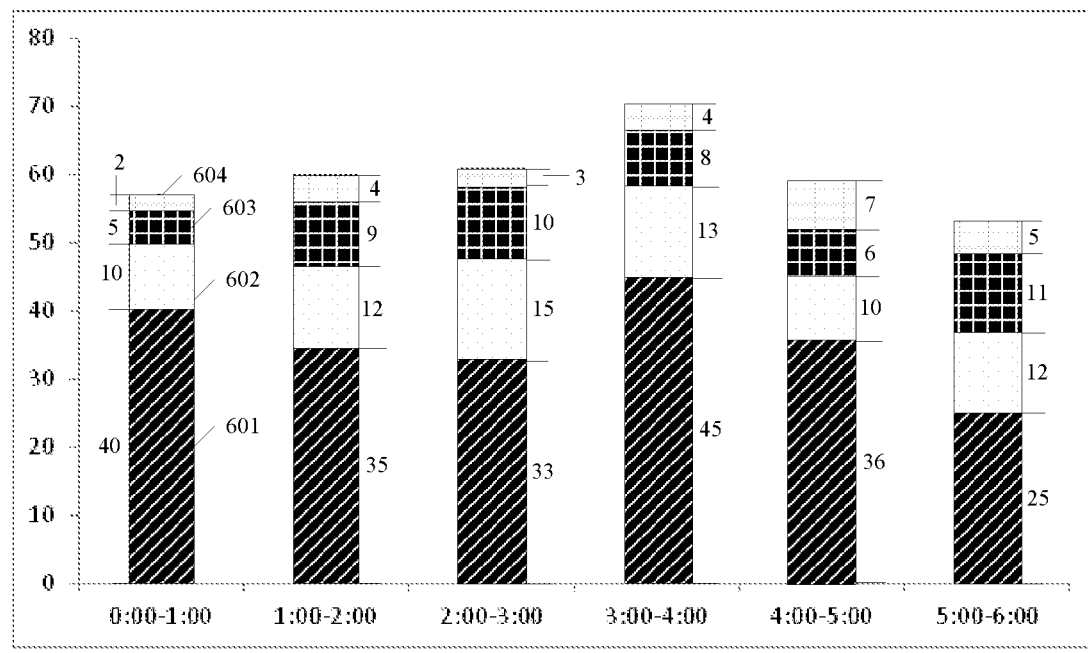
FIG. 6 is a schematic diagram for a statistical result of ventricular premature beat provided by an embodiment of this disclosure.

The above-described monitoring apparatus may graphically display the N group of statistical result. As shown in FIG. 6, FIG. 6 is a graph showing the statistical result of the ventricular premature beat.

In the embodiment of this disclosure, the monitoring apparatus can receive the statistical setting information, perform the statistical analysis for the target parameter according to the statistical setting information, and display the statistical result. Also, the monitoring apparatus can intuitively display the statistical result of the target parameter according to the user's setting information, thus achieving simple operation.

In an optional implementation, after obtaining the N group of statistical result corresponding to the N time interval for each type of the target parameter according to the number of each type of the target parameter in the N group of target parameter result based on the classification rule, the method may further include performing an alarm operation of a target level when it is determined that the statistical result of a target group meets the alarm condition of the target level, where the statistical result of the target group is included in the N group of statistical result.

The above-described monitoring apparatus can perform one or more levels of alarm operation. Different levels of alarm operations are performed when different levels of alarm conditions are met. For example, the monitoring apparatus may include multiple alarm lights, and different levels of alarm operations may light up different alarm lights. For another example, the monitoring apparatus may include one alarm light, which sends out alarms through its different working states. For example, continuous lighting may refer to the first level of alarm, the flash at a first frequency may refer to the second level of alarm, and the flash at a second frequency may refer to the third level of alarm. For another example, the monitoring apparatus may include one alarm light, which sends out alarms through its different working states. For example, the alarm light may emit green light to indicate the first level of alarm, yellow light to indicate the second level of alarm, and red light to indicate the third level of alarm. The alarm operation is not limited in the embodiment of this disclosure.

In an optional implementation, the statistical result of the target group may include the statistical result from the statistical result of a first type of the target parameter to the statistical result of an $M^{th}$ type of the target parameter.

Determining whether the statistical result of the target group meets the alarm condition of the target level may first include comparing the statistical result of an $F^{th}$ type of the target parameter with an alarm threshold corresponding to the $F^{th}$ type of the target parameter, where F is less than or equal to M, M is greater than or equal to 1, and the statistical result of the $F^{th}$ type of the target parameter can be the number or the proportion of the $F^{th}$ type of the target parameters. Determining whether the statistical result of the target group meets the alarm condition of the target level may further include determining whether the statistical result of the $F^{th}$ type of the target parameter is greater than or equal to a target threshold, where the target threshold is the alarm threshold corresponding to the target level.

For example, the target parameter can be ventricular premature beat, and the classification rule can be based on the number of consecutive ventricular premature beat. Correspondingly, the target parameter of ventricular premature beat can be divided into four types: singular ventricular premature beat, two consecutive ventricular premature beats, short consecutive ventricular premature beats, and long consecutive ventricular premature beats. The monitoring apparatus may count the number of these four types of the ventricular premature beats. As shown in FIG. 6, FIG. 6 is a graphical display of the statistical results of the ventricular premature beat, where the reference sign 601 may represent the number of singular ventricular premature beat, the reference sign 602 may represent the number of the two consecutive ventricular premature beats, the reference sign 603 may represent the number of the short consecutive ventricular premature beats, and the reference sign 604 may represent the number of the long consecutive ventricular premature beats. Table 1 below shows a correspondence between the alarm type and the alarm thresholds, in which each alarm type corresponds to a group of alarm thresholds. The correspondence table between the alarm type and the alarm threshold can be preset within the monitoring apparatus or can be set by the user.

TABLE 1

| Alarm Type | Low-level alarm threshold | Medium-level alarm threshold | High-level alarm threshold |
|---|---|---|---|
| Singular ventricular premature beat per hour | 60 | 80 | 100 |
| Two consecutive ventricular premature beats per hour | 20 | 30 | 40 |
| Short consecutive ventricular premature beats per hour | 15 | 20 | 25 |
| Long consecutive ventricular premature beats per hour | 6 | 8 | 10 |

Comparing the statistical result of the $F^{th}$ type of the target parameter with the alarm threshold corresponding to the $F^{th}$ type of the target parameter may refer to comparing whether the statistical result of the $F^{th}$ type of the target parameter is greater than or equal to at least one alarm threshold corresponding to the $F^{th}$ type of the target parameter. Taking the statistical results during the time period of 4 o'clock-5 o'clock as an example, the number of the long consecutive ventricular premature beats is 7, and the low-level alarm is given since the number of the long consecutive ventricular premature beats meets the low-level alarm condition of the long consecutive ventricular premature beats. The monitoring apparatus may detect whether the statistical result of each type of the target parameter meets the alarm condition of the corresponding type. When the statistical result of a certain time period meets two or more alarm conditions, the highest level of alarm operation can be performed. For example, the number of the singular ventricular premature beat in a certain time period is 60, which meets the low-level alarm threshold, the number of the short consecutive ventricular premature beats in the same time period is 21, which meets the medium-level alarm threshold, and thus a medium-level alarm operation will be performed. The above-described ventricular premature may all refer to ventricular premature beat.

In the embodiment of this disclosure, the alarm operation required to be performed can be determined accurately and quickly, and the determination process is simple.

In an optional implementation, the statistical setting information may also include an alarm threshold setting information. The alarm threshold setting information can be used for setting the alarm threshold corresponding to each type of the target parameter.

In the embodiment of this disclosure, the user may set the alarm threshold corresponding to each type of the target parameter through the alarm threshold setting information. For example, the user can set the alarm thresholds in Table 1.

In the embodiment of this disclosure, the monitoring apparatus can set the alarm threshold according to the alarm threshold setting information in the statistical setting information, which can meet the needs of different users and achieve simple operation.

In an optional implementation, before receiving the statistical setting information, the method may further include: acquiring physiological signal and preprocessing the physiological signal; calculate a time-domain characteristic and a frequency-domain characteristic of the pre-processed physiological signal; calculating, based on the time-domain characteristic and the frequency-domain characteristic, to obtain the result of historical physiological parameter.

The above-described monitoring apparatus may acquire the physiological signal of the patient through a physiological signal acquisition device or a physiological signal input module. For example, the monitoring apparatus may acquire ECG signal, blood oxygen signal etc. of the patient. Preprocessing the physiological signal may include filtering out high-frequency noise from the physiological signal, removing baseline drift of the physiological signal, and some other operations, which is not limited in the embodiment of this disclosure. The time-domain characteristic can include QRS wave position, QRS wave interval, QRS wave width and pulse wave position calculated according to the physiological signal. The frequency-domain characteristic can include spectral power distribution and effective signal frequency peak position of the physiological signal. The result of historical physiological parameter may include those physiological parameter results such as heart rate, the number of the ventricular premature beat per minute, and the arrhythmia alarm.

In the embodiment of this disclosure, the monitoring apparatus can perform the preprocessing operation and the characteristic calculation operation on the acquired physiological signal to obtain the result of historical physiological parameter for further storage, which is simple in the implementation.

In an optional implementation, obtaining the N group of target parameter result corresponding to the N time interval from the result of historical physiological parameter can include obtaining the target parameter result within the time range from the result of historical physiological parameter, segmenting the target parameter result within the time range according to the time interval to obtain the N group of target parameter result corresponding to the N time interval.

In an optional embodiment, displaying the N group of statistical result may include graphically displaying the N group of statistical result.

For example, when the time range is 6 hours and the time interval is 1 hour, the monitoring apparatus can obtain the physiological parameter result of this time range, and segment the physiological parameter result of this time range into 6 segments, where each segment is the physiological parameter result corresponding to one time interval.

The graphical display for representing the N group of statistical result can include a bar chart, a line chart, a pie chart, a doughnut chart and an area chart, which is not limited in the embodiments of this disclosure.

In the embodiment of this disclosure, the monitoring apparatus can calculate the statistical result of the target parameter according to the statistical setting information, so as to obtain the statistical result in respective time intervals when the statistical setting information is executed, which is simple in the implementation.

In a first embodiment of this disclosure, the physiological signal monitoring of a certain patient is started at 0:00, where the physiological signal monitoring includes ECG monitoring and blood oxygen monitoring. This patient is an arrhythmia patient, and there are various types of ventricular premature beats in the ECG signal. The physiological signal analysis module of the monitoring apparatus may keep analyzing the ECG signal and calculate the following ECG parameters: QRS wave classification result (normal heart beat and ventricular premature beat), QRS classification template type, QRS wave interval, heart rate and arrhythmia alarm. For this patient, there is also increase and decrease in his blood oxygen levels, and the physiological signal analysis module may also keep analyzing the blood oxygen signal to calculate the following blood oxygen parameters: pulse rate and blood oxygen saturation.

The current time instant is 6:00 and the user wants to know the statistics of the physiological parameters every hour in the incoming 6 hours. That is, the statistical information is set as follows: the time range for statistical analysis is 0:00 to 6:00, and the time interval for statistical analysis is 1 hour.

If the physiological parameter selected by the user is the ventricular premature beat, the classification rule can be based on the number of the consecutive ventricular premature beat, and the selected physiological parameter can be divided into four types: singular ventricular premature beat (1 V), two consecutive ventricular premature beats (2 V), short consecutive ventricular premature beats (3 To 5 V), and long consecutive ventricular premature beats (greater than 5 V). FIG. 6 is a schematic diagram for the statistical result of the ventricular premature beat, where the reference sign 601 may represent the number of the singular ventricular premature beat, the reference sign 602 may represent the number of two consecutive ventricular premature beats, the reference sign 603 may represent the number of short consecutive ventricular premature beats, and the reference sign 604 may represent the number of the long consecutive ventricular premature beat.

Figure 7:
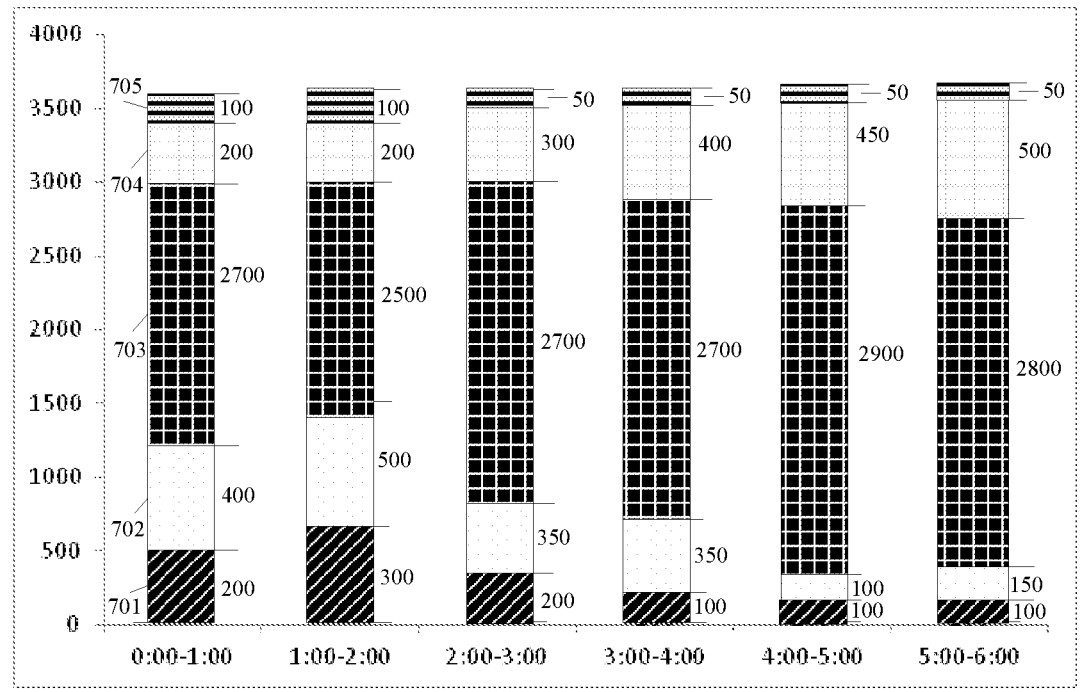
FIG. 7 is a schematic diagram for a statistical result of heart rate or pulse rate provided by an embodiment of this disclosure.

If the physiological parameter selected by the user is the heart rate or the pulse rate, the classification rule can be based on the range of the heart rate or the pulse rate, and the selected physiological parameter can be divided into five types: extreme bradycardia (HR<35 bpm), bradycardia (35 bpm<=HR<50 bpm), normal (50 bpm<=HR<=120 bpm), tachycardia (120 bpm<HR<=160 bpm) and extreme tachycardia (HR>160 bpm). FIG. 7 is a schematic diagram for the statistical result of the heart rate/pulse rate, where the reference sign 701 may represent the number of the extreme bradycardia, the reference sign 702 may represent the number of the bradycardia, the reference sign 703 may represent the number of the normal heartbeat, the reference sign 704 may represent the number of the tachycardia, and the reference sign 705 may represent the number of the extreme tachycardia.

Figure 8:
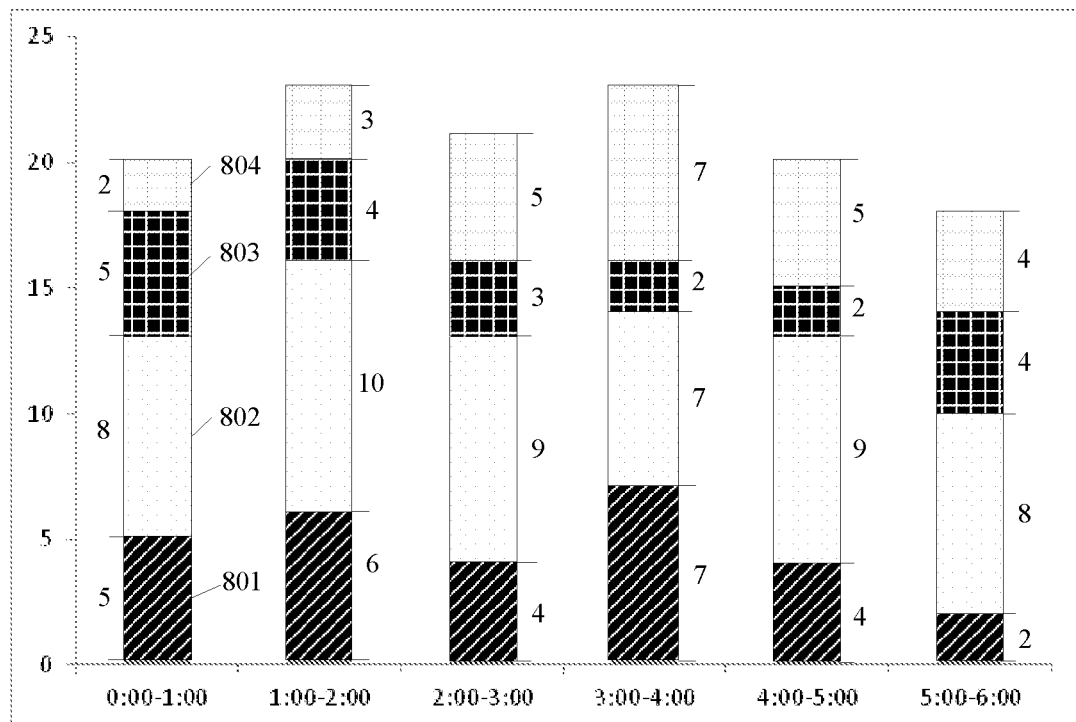
FIG. 8 is a schematic diagram for a statistical result of the number of arrhythmia alarm provided by an embodiment of this disclosure.

If the physiological parameter selected by the user is the arrhythmia alarm event, the classification rule can be based on the alarm level, and thus the selected physiological parameter can be divided into four types: high-level alarm (cardiac arrest, ventricular fibrillation, ventricular tachycardia, ventricular bradycardia, extreme tachycardia, extreme bradycardia), medium-level alarm (R on T, polymorphic ventricular premature beat, ventricular premature beat bigeminy, ventricular premature beat trigeminy, bradycardia, tachycardia, unsustainable ventricular tachycardia, ventricular rhythm), low-level alarm (consecutive ventricular premature beat, heartbeat pause), and prompting alarm (two consecutive ventricular premature beat, singular ventricular premature beat, pacemaker not captured, pacemaker not paced, dropped beat, irregular rhythm, atrial fibrillation). FIG. 8 is a schematic diagram for the statistical result of the number of arrhythmia alarm, where the reference sign 801 may represent the number of the high-level alarm, the reference sign 802 may represent the number of the medium-level alarm, the reference sign 803 may represent the number of the low-level alarm, and the reference sign 804 may represent the number of the prompting alarm.

Figure 9:
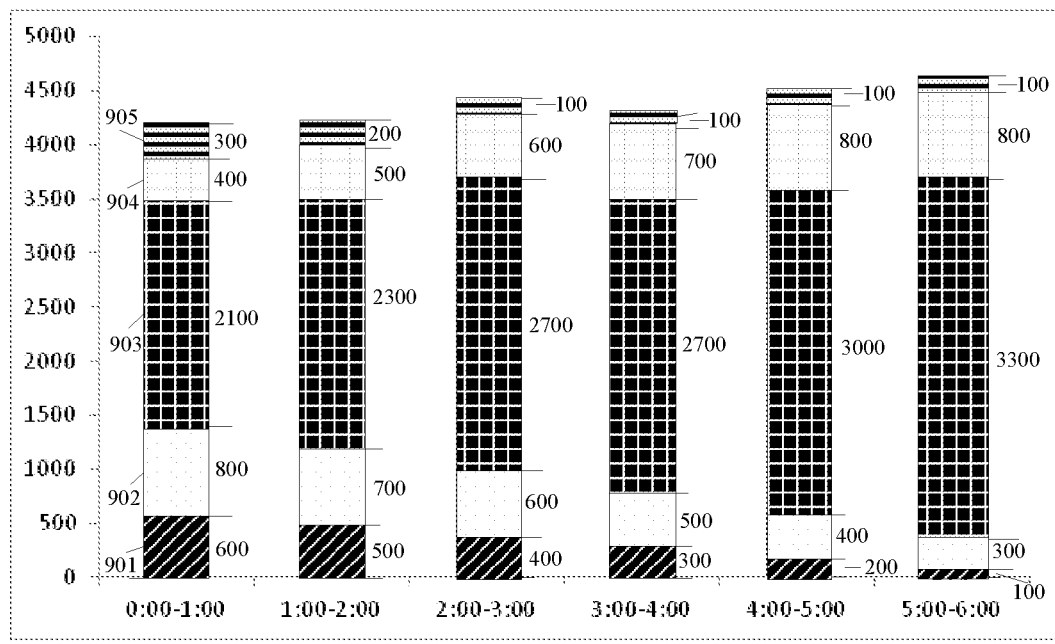
FIG. 9 is a schematic diagram for a statistical result of QRS wave interval provided by an embodiment of this disclosure.

If the physiological parameter selected by the user is the QRS wave interval (the corresponding unit is ms), the classification rule can be based on the range of the heart rate corresponding to the QRS wave interval (conversion formula: 60*1000/QRS wave interval), and thus the selected physiological parameter can be divided into five types: extreme bradycardia (HR<35 bpm), bradycardia (35 bpm<=HR<50 bpm), normal (50 bpm<=HR<=120 bpm), tachycardia (120 bpm<HR<=160 bpm), and extreme tachycardia (HR>160 bpm), FIG. 9 is a schematic diagram for the statistical result of the QRS wave interval, where the reference sign 901 may represent the number of the extreme bradycardia, the reference sign 902 may represent the number of the bradycardia, the reference sign 903 may represent the number of the normal heartbeat, the reference sign 904 may represent the number of the tachycardia, and the reference sign 905 may represent the number of the extreme tachycardia.

Figure 10:
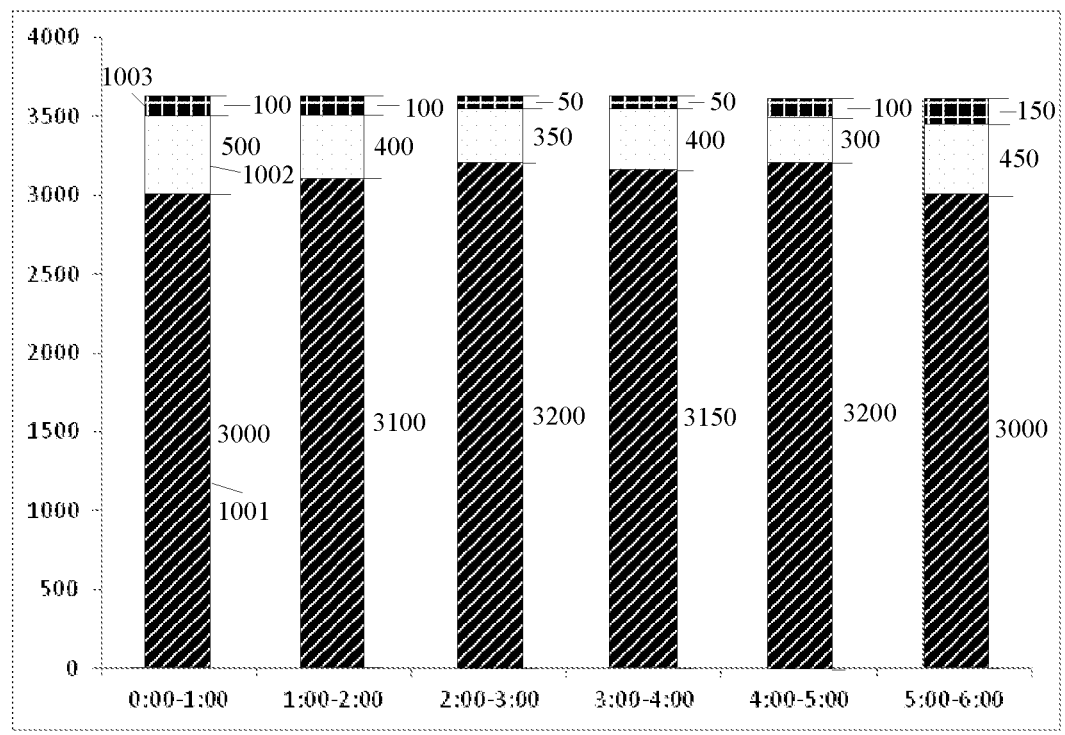
FIG. 10 is a schematic diagram for a statistical result of a blood oxygen saturation provided by an embodiment of this disclosure.

If the physiological parameter selected by the user is the blood oxygen saturation, the classification rule can be based on the range of the blood oxygen saturation, and the selected physiological parameter can be divided into three types: normal blood oxygen (SpO2>=90%), medium blood oxygen (80%<=SpO2<90%), and low blood oxygen (SpO2<80%). FIG. 10 is a schematic diagram for the statistical result of the blood oxygen saturation, where the reference sign 1001 may represent the number of the normal blood oxygen, the reference sign 1002 may represent the number of the medium blood oxygen, and the reference sign 1003 may represent the number of the low blood oxygen.

Figure 11:
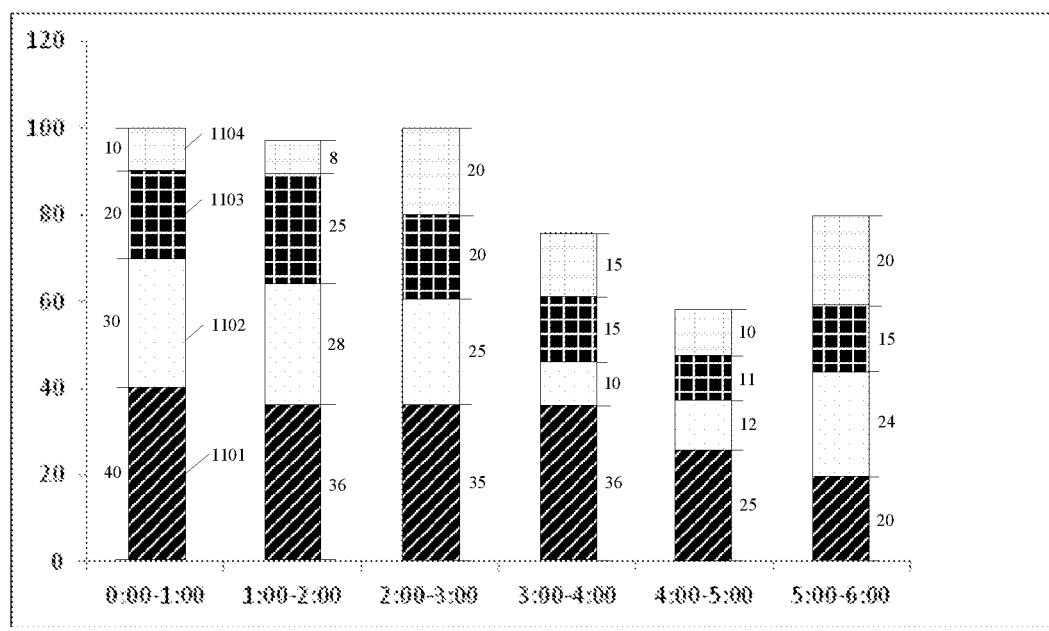
FIG. 11 is a schematic diagram for a statistical result of a type of ventricular premature beat template provided by an embodiment of the this disclosure.

If the physiological parameter selected by the user is the classification template type of the ventricular premature beat, the classification rule can be based on a serial number of the template type, and thus the selected physiological parameter can be divided into N template type (from template 1 to template N). In an embodiment, there can be four types of ventricular premature beat templates for the monitored patient during the time period, namely template 1 to template 4 and 4 template types in total. The graphical display output by the physiological parameter statistics display module is shown in FIG. 11. FIG. 11 is a schematic diagram for the statistical result of the template type of the ventricular premature beat, where the reference sign 1101 may represent the number of the template 4, the reference sign 1102 may represent the number of the template 3, the reference sign 1103 may represent the number of the template 2, and the reference sign 1104 may represent the number of the template 1.

If the user selects other physiological parameter, the classification can be performed according to the value range or the type of the classification rule set by the user. The physiological parameter statistics display module can output the graphical statistical result.

In the embodiment of this disclosure, the monitoring apparatus can intuitively display the statistical result of the target parameter according to the setting information of the user, and thus the operation is simple.

Figure 12:
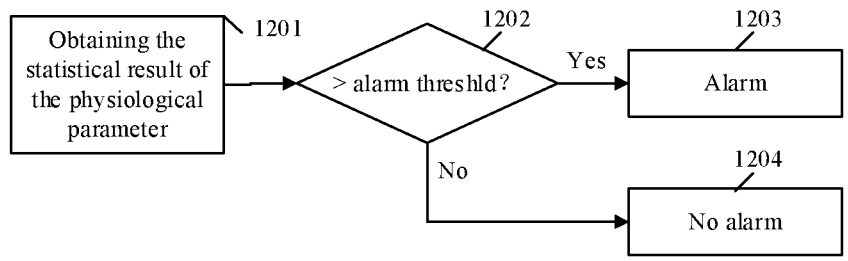
FIG. 12 is a flowchart of an alarm method provided by an embodiment of this disclosure.

In a second embodiment of this disclosure, the structural schematic diagram of the monitoring apparatus in the second embodiment can be seen in FIG. 1. Compared with the first embodiment, an alarm module is further included in the second embodiment. FIG. 12 is a flowchart for an alarm method provided by the second embodiment of this disclosure. An alarm module of the monitoring apparatus may use the physiological parameter statistical information and a preset alarm threshold to give an alarm result. The alarm method provided by this embodiment of this disclosure is shown in FIG. 12 and can include steps 1201 to 1204.

In step 1201, the statistical result of the physiological parameter can be obtained.

In step 1202, it can be determined whether the statistical result of the physiological parameter exceeds the alarm threshold. When the statistical result of the physiological parameter exceeds the alarm threshold, the step 1203 may be performed; when the statistical result of the physiological parameter fails to exceed the alarm threshold, the step 1204 may be performed.

In step 1203, the alarm operation may be performed.

In step 1204, the alarm operation may not be performed.

The object of the alarm can be the statistical information of the physiological parameter of the patient from 0 o'clock to 6 o'clock in the first embodiment. Taking the ventricular premature beat as an example of the physiological parameter to be alarmed, the alarm threshold set by the user is shown in Table 1. It can be seen that in the time period of 4 o'clock to 5 o'clock, the number of the long consecutive ventricular premature beat is 7, which meets the low-level alarm condition of the long consecutive ventricular premature beat. Thus, a low-level alarm can be provided.

In the embodiment of this disclosure, the monitoring apparatus can determine the satisfied alarm condition according to the physiological parameter statistical information and the preset alarm threshold, and perform the corresponding alarm operation to notify the user in time.

Figure 13:
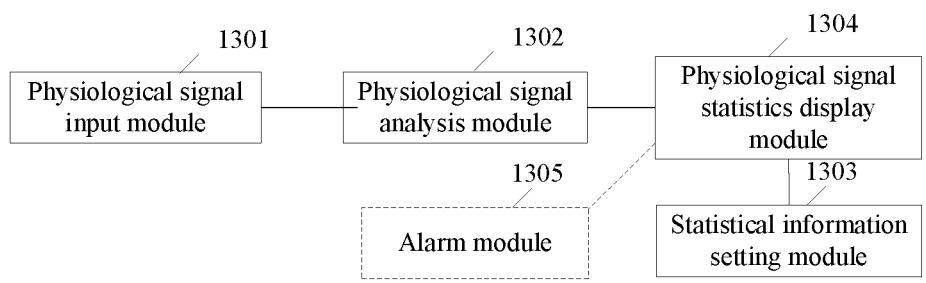
FIG. 13 is a schematic structural diagram for a monitoring apparatus provided by another embodiment of this disclosure.

FIG. 13 is a structural diagram for another monitoring apparatus provided by an embodiment of the disclosure, where the monitoring apparatus may include a statistical information setting module 1303 and a physiological parameter statistics display module 1304.

The statistical information setting module 1303 may be configured to receive and/or extract statistical setting information, which may include a time range, a time interval, a classification rule and a target parameter.

The physiological parameter statistics display module 1304 may be configured to obtain N group of target parameter result corresponding to the N time interval from a result of historical physiological parameter, where the N time interval is included in the time range, and the N group of target parameter result may refer to a physiological parameter result corresponding to the target parameter in the result of historical physiological parameter result. The physiological parameter statistics display module 1304 may also be configured to count a number of each type of the target parameter in the N group of target parameter results according to the classification rule, so as to obtain N group of statistical results corresponding to the N time interval for each type of the target parameter. Also, the physiological parameter statistics display module 1304 may be configured to display the N group of statistical result.

The specific implementing method is the same as that in FIG. 5 and therefor is not described in further details.

In an alternative implementation, as shown in FIG. 13, the above-described monitoring apparatus may further include an alarm module 1305 that is configured to perform an alarm operation of a target level when determining that the statistical result of the target group satisfies an alarm condition of the target level, where the statistical result of the target group is included in the N group of statistical result.

In an alternative implementation, the statistical result of the target group may include a statistical result from a statistical result of a first type of the target parameter to a statistical result of an $M^{th}$ type of the target parameter.

The alarming module 1305 may be configured to compare a statistical result of an $F^{th}$ type of the target parameter with an alarm threshold corresponding to the $F^{th}$ type of the target parameter, where F is less than or equal to M, M is greater than or equal to 1, and the statistical results of the $F^{th}$ type of the target parameter are the number or the proportion of the $F^{th}$ type of the target parameter. The alarm module 1305 may further be configured to determine that the statistical result of the $F^{th}$ type of the target parameter is greater than or equal to a target threshold, where the target threshold is an alarm threshold corresponding to the target level.

In the embodiments of this disclosure, the alarm operations needed to be executed can be accurately and rapidly determined, and the realization is simple.

In an alternative implementation, the statistical setting information may further include the classification rule, which defines one or more types of the target parameters and/or corresponding numerical range for each type of the target parameter.

The physiological parameter statistics display module 1304 may be configured to count the number of each type of the target parameter in the N group of physiological parameter result according to the classification rule, so as to obtain N group of statistical result corresponding to the N time interval for each type of the target parameter.

In the embodiments of this disclosure, the users are allowed to set the classification rules according to their own needs, instead of adopting fixed classification rule. Therefore, the needs of different users can be met.

In an alternative implementation, the statistical setting information may further include alarm threshold setting information used to set the alarm threshold corresponding to each type of the target parameter.

In the embodiment of this disclosure, the monitoring apparatus can set the alarm threshold according to the alarm threshold setting information in the statistical setting information. Therefore, the needs of different users can be met, and the operation is simple.

In an alternative implementation, the monitoring apparatus may further include a physiological signal input module 1301 configured to acquire physiological signal; and a physiological signal analysis module 1302 configured to preprocess the physiological signal, calculate time-domain characteristic and frequency-domain characteristic of the pre-processed physiological signal; calculate based on the time-domain characteristic and the frequency-domain characteristics to obtain the result of historical physiological parameter.

In the embodiments of this disclosure, the monitoring apparatus may preprocess the collected physiological signal and calculate the time-domain characteristics and the frequency-domain characteristic of the preprocessed physiological signal, so as to obtain and further store the result of historical physiological parameter. The implementation is simple.

In an alternative embodiment, the above-described physiological parameter statistics display module 1304 may be configured to obtain the target parameter result in the time range from the result of historical physiological parameter; segment the target parameter result in the time range according to the time interval, obtain the N group of target parameter result corresponding to the N time interval; and graphically display the N group of statistical result.

In the embodiments of this disclosure, the monitoring apparatus can count the statistical result of the target parameter according to the statistical setting information, so as to obtain the statistical result in respective time intervals where the statistical setting information is executed, which is simple in implementation.

Figure 14:
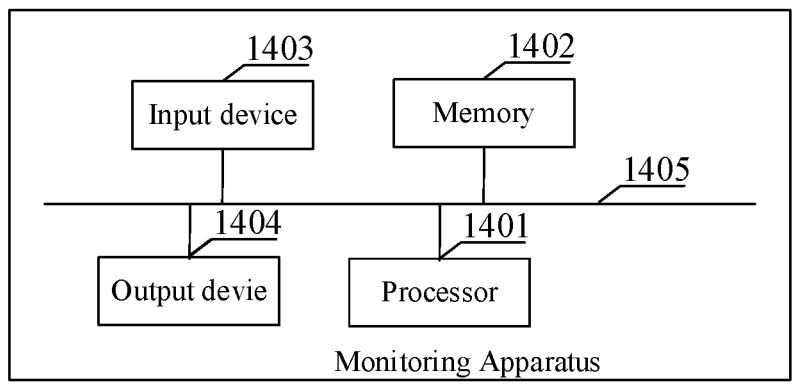
FIG. 14 is a schematic structural diagram for a monitoring apparatus provided by another embodiment of this disclosure.

FIG. 14 shows a monitoring apparatus provided by an embodiment of this disclosure. The monitoring apparatus may include a processor 1401, a memory 1402, an input device 1403 and an output device 1404. The processor 401, the memory 402, the input device 1403 and the output device 1404 can be connected with each other through a bus.

The memory 1402 includes but is not limited to a Random Access Memory (RAM), a Read-Only Memory (ROM), a Erasable Programmable Read-Only Memory (EPROM), or a Compact Disc Read-Only Memory (CD-ROM). The Memory 1402 is used for related instructions and data. The input device 1403 is used to input statistical device information. The output device 1404 is used to display the statistical result.

The processor 1401 may be one or more central processing units (CPUs). In the case that the processor 1401 is one CPU, the CPU may be either a single-core CPU or a multi-core CPU.

The processor 1401 of the monitoring apparatus may be used to read the program code stored in the memory 1402, so as to perform the following operation: receive and/or extract statistical setting information including a time range, a time interval, a classification rule and a target parameter, the classification rule defining one or more types of the target parameter; obtain N group of target parameter result corresponding to the N time interval from a result of historical physiological parameter, where the N time interval is included in the time range, and the N group of target parameter result may refer to a physiological parameter result corresponding to the target parameter in the result of historical physiological parameter result; count a number of each type of the target parameter in the N group of target parameter result according to the classification rule, obtain N group of statistical result corresponding to the N time intervals for each type of the target parameter; and control to display the N group of statistical result.

It should be noted that the implementation of each operation may also correspond to the corresponding description of the method embodiment shown in FIG. 5.

An embodiment of this disclosure may provide a computer readable storage medium, wherein the computer readable storage medium may store a computer program which is implemented by a processor to: receive and/or extract statistical setting information including a time range, a time interval, a classification rule and a target parameter, the classification rule defining one or more types of the target parameter; obtain N group of target parameter result corresponding to the N time interval from a result of historical physiological parameter, where the N time interval is included in the time range, and the N group of target parameter result may refer to a physiological parameter result corresponding to the target parameter in the result of historical physiological parameter result; count a number of each type of the target parameter in the N group of target parameter result according to the classification rule, obtain N group of statistical result corresponding to the N time intervals for each type of the target parameter; and control to display the N group of statistical result.

The computer readable storage medium may be the internal storage unit of the monitoring apparatus in any of the foregoing embodiments, such as the hard disk or the memory of the monitoring apparatus. The computer readable storage medium may also be external storage device of the monitoring apparatus, such as plug-in hard disk, Smart Media Card (SMC), Secure Digital (SD) Card, Flash Card, etc.

Ordinary technicians in this field can understand the process of realizing all or part of the above embodiments, which can be completed by a computer program to instruct the relevant hardware, which can be stored in a computer-readable storage medium, and which, when executed, may include a process such as the above embodiments of each method. The storage media mentioned above include: ROM or random storage memory RAM, disk or optical disk and other media that can store program code.

The above is only the specific implementation mode of the disclosure, but the protection scope of the disclosure is not limited to this. Any technical personnel familiar with the technical field can easily think of various equivalent modifications or substitutions within the scope of the technology disclosed by the disclosure, which shall be covered by the protection scope of the disclosure. Therefore, the protection scope of the disclosure shall be subject to the protection scope of the claim.

What is claimed is:

1. A statistical display method of physiological parameter(s) in a monitoring apparatus, comprising:
receiving statistical setting information, which comprises a time range, a time interval, a classification rule and a target parameter, the classification rule defining one or more types of the target parameter;
obtaining N group of target parameter result corresponding to N time interval from a result of historical physiological parameter, wherein the N time interval is included in the time range, and the N group of target parameter result is a physiological parameter result corresponding to the target parameter in the result of historical physiological parameter;
counting a number of each type of the target parameter in the N group of target parameter result according to the classification rule, and obtaining N group of statistical result corresponding to the N time interval for each type of the target parameter, wherein each group of statistical result is indicative of the counted numbers of the types of target parameter within the corresponding time interval; and
displaying the N group of statistical result with respect to the N time intervals, wherein for each time interval, a distribution of the counted numbers of the types of target parameter within that time interval is displayed.

2. The statistical display method of claim 1, wherein after counting a number of each type of the target parameter in the N group of target parameter result according to the classification rule, and obtaining N group of statistical result corresponding to the N time interval for each type of the target parameter, the method further comprises:
performing an alarm operation of a target level, when determining that the statistical result of a target group satisfies an alarm condition of the target level, wherein the statistical result of the target group is included in the N group of statistical result.

3. The statistical display method of claim 2, wherein the statistical result of the target group comprises a statistical result from a statistical result of a first type of the target parameter to a statistical result of an $M^{th}$ type of the target parameter; and
wherein determining that the statistical result of a target group satisfies an alarm condition of the target level comprising:
comparing a statistical result of an $F^{th}$ type of the target parameter with an alarm threshold corresponding to the $F^{th}$ type of the target parameter, wherein F is less than or equal to M, both F and M are greater than or equal to 1, and the statistical result of the $F^{th}$ type of the target parameter is a number or a proportion of the $F^{th}$ type of the target parameter; and
determining that the statistical result of the $F^{th}$ type of the target parameter is greater than or equal to a target threshold, wherein the target threshold is an alarm threshold corresponding to the target level.

4. The statistical display method of claim 3, wherein the statistical setting information further comprises alarm threshold setting information used to set the alarm threshold corresponding to each type of the target parameter.

5. The statistical display method of claim 1, before receiving statistical setting information, the method further comprises:
acquiring physiological signal and preprocessing the physiological signal;
calculating time-domain characteristic and frequency-domain characteristic of the pre-processed physiological signal; and
calculating based on the time-domain characteristic and the frequency-domain characteristic to obtain the result of historical physiological parameter.

6. The statistical display method of claim 5, wherein obtaining N group of target parameter result corresponding to N time interval from a result of historical physiological parameter further comprises:
obtaining the target parameter result in the time range from the result of historical physiological parameter;
segmenting the target parameter result in the time range according to the time interval, and obtaining the N group of target parameter result corresponding to the N time interval; and
wherein displaying the N group of statistical result comprises graphically displaying the N group of statistical result.

7. The statistical display method of claim 1, wherein displaying the N group of statistical result comprises displaying the N group of statistical result through at least one of a bar chart, a line chart, a pie chart, a doughnut chart and an area chart.

8. The statistical display method of claim 1, wherein the target parameter is a ventricular premature beat, and the classification rule is based on a number of a consecutive ventricular premature beat; or, the target parameter is a QRS wave interval, and the classification rule is based on a number of a consecutive ventricular premature beat; or the target parameter is a heart rate or a pulse rate, and the classification rule is based on a range of the heart rate or the pulse rate; or the target parameter is an arrhythmia alarm event, and the classification rule is based on an alarm level; or the target parameter is a blood oxygen saturation, and the classification rule is based on a range of the blood oxygen saturation; or the classification rule is based on a serial number of a template type.

9. A monitoring apparatus, comprising:
an input device configured to receive statistical setting information, which comprises a time range, a time interval, a classification rule and a target parameter;
a processor that is configured to:
obtain N group of target parameter result corresponding to N time interval from a result of historical physiological parameter, wherein the N time interval is included in the time range, and the N group of target parameter result is a physiological parameter result corresponding to the target parameter in the result of historical physiological parameter; and
count a number of each type of the target parameter in the N group of target parameter result according to the classification rule, and obtain N group of statistical result corresponding to the N time interval for each type of the target parameter, wherein each group of statistical result is indicative of the counted numbers of the types of target parameter within the corresponding time interval; and a display that displays the N group of statistical result with respect to the N time intervals, wherein for each time interval, a distribution of the counted numbers of the types of target parameter within that time interval is displayed.

10. The monitoring apparatus of claim 9, wherein the processor is further configured to:

perform an alarm operation of a target level, when determining that the statistical result of a target group satisfies an alarm condition of the target level, wherein the statistical result of the target group is included in the N group of statistical result.

11. The monitoring apparatus of claim 10, the statistical result of the target group comprises a statistical result from a statistical result of a first type of the target parameter to a statistical result of an $M^{th}$ type of the target parameter; and compare a statistical result of an $F^{th}$ type of the target parameter with an alarm threshold corresponding to the $F^{th}$ type of the target parameter, wherein F is less than or equal to M, both F and M are greater than or equal to 1, and the statistical result of the $F^{th}$ type of the target parameter is a number or a proportion of the $F^{th}$ type of the target parameter; and determine that the statistical result of the $F^{th}$ type of the target parameter is greater than or equal to a target threshold, wherein the target threshold is an alarm threshold corresponding to the target level.

12. The monitoring apparatus of claim 11, wherein the statistical setting information further comprises alarm threshold setting information used to set the alarm threshold corresponding to each type of the target parameter.

13. The monitoring apparatus of claim 9, further comprises:

a physiological signal input device, configured to acquire physiological signal; and wherein the processor is further configured to preprocess the physiological signals, calculate time-domain characteristic and frequency-domain characteristic of the preprocessed physiological signal; calculate based on the time-domain characteristic and the frequency-domain characteristic to obtain the result of historical physiological parameter.

14. The monitoring apparatus of claim 13, wherein the processor is further configured to:

obtain the target parameter result in the time range from the result of historical physiological parameter;

segment the target parameter result in the time range according to the time interval, and obtain the N group of target parameter result corresponding to the N time interval; and the display is further configured to graphically display the N group of statistical result.

15. The monitoring apparatus of claim 9, wherein the display is further configured to display the N group of statistical result through at least one of a bar chart, a line chart, a pie chart, a doughnut chart and an area chart.

16. The monitoring apparatus of claim 9, wherein the target parameter is a ventricular premature beat, and the classification rule is based on a number of a consecutive ventricular premature beat; or, the target parameter is a QRS wave interval, and the classification rule is based on a number of a consecutive ventricular premature beat; or the target parameter is a heart rate or a pulse rate, and the classification rule is based on a range of the heart rate or the pulse rate; or the target parameter is an arrhythmia alarm event, and the classification rule is based on an alarm level; or the target parameter is a blood oxygen saturation, and the classification rule is based on a range of the blood oxygen saturation; or the classification rule is based on a serial number of a template type.

17. A monitoring apparatus, comprising an input device, a processor and a display; Wherein:

the input device is configured to receive statistical setting information, which comprises a time range, a time interval, a classification rule and a target parameter;

the processor is configured to obtain a plurality of groups of target parameter results corresponding to a plurality of time intervals from a result of historical physiological parameter, wherein the plurality of time intervals are included in the time range, and the plurality of groups of target parameter results are physiological parameter results corresponding to the target parameter in the result of historical physiological parameter, and the processor is further configured to obtain a plurality of groups of statistical results based on the plurality of groups of target parameter results, and control the display to display the plurality of groups of statistical results, wherein each group of statistical result is indicative of the counted numbers of the types of target parameter within the corresponding time interval; and wherein the display is configured to display the plurality of groups of statistical results by a plurality of charts, wherein the plurality of charts are separated from each other and correspond to the respective plurality of time intervals within the time range;

each chart shows a distribution of the counted numbers of the types of the target parameter within the corresponding time interval; and each chat is divided into one or more portions, each portion corresponding to each type of the target parameter that is classified according to the classification rule.

18. The monitoring apparatus of claim 17, wherein the display is further configured to display, in each chart, a numeric character representing the counted number of each type of the target parameter in the corresponding time interval.

19. The monitoring apparatus claim 17, wherein the one or more portions in each chart are displayed through different patterns.

20. The monitoring apparatus of claim 17, wherein the target parameter is a ventricular premature beat, the classification rule defines the types of the target parameter based on a number of a consecutive ventricular premature beat, and the one or more portions of each chart corresponds to at least one of singular ventricular premature beat, two consecutive ventricular premature beats, short consecutive ventricular premature beats, and long consecutive ventricular premature beats;

or, the target parameter is a QRS wave interval, the classification rule defines the types of the target parameter based on a number of a consecutive ventricular premature beat, and the one or more portions of each chart correspond to at least one of extreme bradycardia, bradycardia, normal, tachycardia, and extreme tachycardia;

or, the target parameter is a heart rate or a pulse rate, the classification rule defines the types of the target parameter based on a range of the heart rate or the pulse rate, and the one or more portions of each chart correspond to at least one of extreme bradycardia, bradycardia, normal, tachycardia and extreme tachycardia;

or, the target parameter is an arrhythmia alarm event, the classification rule defines the types of the target parameter based on an alarm level, and the one or more portions of each chart correspond to at least one of high-level alarm, medium-level alarm and low-level alarm;

or, the target parameter is a blood oxygen saturation, the classification rule defines the types of the target parameter based on a range of the blood oxygen saturation, and the one or more portions of each chart correspond to at least one of normal blood oxygen, medium blood oxygen, and low blood oxygen;

or the classification rule defines the types of the target parameter based on a serial number of a template type, and the one or more portions of each chart correspond to one or more template type.

\* \* \* \* \*